(12) United States Patent
Massaro (10) Patent No.: US 7,438,859 B2
(45) Date of Patent: Oct. 21, 2008

(54) METHOD AND APPARATUS FOR LASER IMPULSE SAMPLE DEPOSITION

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 918 days.

(21) Appl. No.: 10/750,377

(22) Filed: Dec. 31, 2003

(65) Prior Publication Data
US 2005/0148095 A1 Jul. 7, 2005

(51) Int. Cl.
B01L 3/02 (2006.01)
(52) U.S. Cl. .................. 422/100; 422/99; 422/101; 436/180; 250/288
(58) Field of Classification Search ........... 422/99–101; 436/180; 250/288
See application file for complete search history.

(56) References Cited

U.S. PATENT DOCUMENTS 5,998,129 A  12/1999  Schuetze et al.
6,423,966 B2 *  7/2002  Hillenkamp et al. ........ 250/288

FOREIGN PATENT DOCUMENTS

| EP | 1096250 A3 | 5/2001 |
| WO | WO9701085 A1 | 1/1997 |
| WO | WO0247820 A2 | 6/2002 |
| WO | WO02062475 A1 | 8/2002 |
| WO | WO02066550 A1 | 8/2002 |

OTHER PUBLICATIONS

Darfler et al., "High Throughput Protein Expression Profiling Using Archival Tissue", poster from "BioChips 2003" conference, Jun. 11-13, 2003, Boston, MA.
Darfler et al., "High Throughput Protein Expression Profiling Using Archival Tissue", poster from "Protein Biomarkers" conference, Aug. 25-26, 2003, Philadelphia, PA.
Darfler et al., "High Throughput Protein Expression Profiling Using Archival Tissue", poster from "Genomics on Target" conference, Oct. 7-10, 2003, Boston, MA.
Tseng, "Micro-Droplet Generations", Mems Handbook, CRC Press, 2001.
Pique et al. "A Novel Laser Transfer Process For Direct Writing Of Electronic And Sensor Materials", Applied Physics A; Materials Science And Processing, Springer Verlag, Berlin, DE, vol. 69, No. Suppl. 1999, pp. S279-S284, XP008001495 ISSN; 0947-8396.
International Search Report PCT/US2004/043790 dated May 6, 2005.

* cited by examiner

Primary Examiner—Jill Warden
Assistant Examiner—Jyoti Nagpaul
(74) Attorney, Agent, or Firm—Wolf, Greenfield & Sacks, P.C.

(57) ABSTRACT

A sample material, such as a liquid including genomic or proteomic materials, may be deposited on a work surface based on illumination of a sample transfer device by an illumination beam. Illumination of the sample transfer device may cause a portion of the sample transfer device to move and thereby cause separation of a portion of the sample material from the sample transfer device and deposition on a work surface. Illumination may cause an energy transfer from the beam to the sample material to thereby cause deposition of the sample material.

28 Claims, 4 Drawing Sheets

METHOD AND APPARATUS FOR LASER IMPULSE SAMPLE DEPOSITION

BACKGROUND OF INVENTION

1. Field of Invention

This invention relates to deposition of sample materials using a laser or other illumination beam.

2. Description of Related Art

Manipulation of material samples is important in a variety of fields, such as in automated proteomic, genomic, and other biotech-related research. Commonly, material samples are handled in liquid form using a variety of different types of liquid handling apparatus, such as pipettors, robotically-manipulated liquid handling tools, spotting devices, etc. To improve processing times, sample density or other features, particularly in automated research operations, sample sizes have been made progressively smaller and smaller. In some case, standard liquid handling apparatus, such as hand-held pipettors, are not suitable for manipulating small sample volumes, such as nanoliter-sized samples.

SUMMARY OF INVENTION

In one aspect of the invention, a sample may be deposited on a work surface based on an illumination beam being incident on a sample transfer device. For example, a liquid material may be positioned on or near a sample transfer device, and when the sample transfer device is illuminated by an illumination beam, at least a portion of the sample material may be transferred to a work surface. By controlling the deposition of samples based on an illumination beam, the size and/or position of the deposited sample on the work surface may be closely controlled.

In one aspect of the invention, a sample depositing system includes an illumination source that forms an illumination beam. For example, the illumination source may be or include a laser, such as a YAG laser. A sample transfer device may carry a sample material to be deposited on a work surface. The sample transfer device may include at least one layer of a material that is relatively transparent to the illumination beam, such as quartz, another inorganic material or other plastic material. The sample transfer device may also include a layer of opaque or transmission-resistant material, such as a layer of nickel or aluminum, a plastic material such as mylar, or other material. Illumination of a portion of the sample transfer device by the illumination beam may cause a portion of the sample material carried by the sample transfer device to be separated from the sample transfer device and deposited on a work surface. The mechanism by which the portion of sample material is separated from the sample transfer device may vary in different ways. For example, in one aspect of the invention, illumination of the sample transfer device by the illumination beam may cause uneven heating and/or expansion in portions of the sample transfer device. This uneven heating/expansion can cause the sample transfer device to buckle or otherwise move rapidly, releasing a portion of the sample carried by the sample transfer device. However, sample deposition does not result from the separation of a portion of the sample transfer device adjacent the sample material that carries sample material with it.

In another aspect of the invention, illumination of the sample transfer device can cause localized heating of a portion of the sample transfer device and/or the sample material. This localized heating may cause a rapid expansion, e.g., caused by vaporization of a portion of the sample transfer device and/or the sample material. This rapid expansion may cause a portion of the sample material to be separated from the sample transfer device and deposited on a work surface.

In another aspect of the invention, illumination of the sample transfer device and/or the sample material may transfer kinetic or other energy from the illumination beam to a portion of the sample material, causing the portion of sample material to be separated from the sample transfer device. For example, the illumination beam may cause bonds in the sample material and/or between the sample material and the sample transfer device to be broken and release energy, thereby causing deposition of a portion of the sample material.

In one aspect of the invention, a sample depositing system includes an illumination source that forms an illumination beam, and a sample transfer device that receives the illumination beam from the illumination source. A sample material may be carried by the sample transfer device, and a controller may cause the illumination source to illuminate the sample transfer device and thereby cause at least a portion of the sample material carried by the sample transfer device to be controllably separated from the transfer device and deposited on a work surface. The portion of sample material may be deposited without requiring a portion of the sample transfer device positioned adjacent the sample material to separate from the sample transfer device.

In another aspect of the invention, a method for depositing a sample material includes providing a sample material on a sample transfer device, and illuminating the sample transfer device with an illumination beam. At least a portion of the sample material may be caused to be separated from the sample transfer device and deposited on a work surface in response to illumination of the illumination beam. The portion of the sample material may be deposited without requiring a portion of the surface positioned adjacent the sample material to separate from the sample transfer device.

These and other aspects of the invention will be apparent and/or obvious from the following detailed description and appended claims.

BRIEF DESCRIPTION OF DRAWINGS

Aspects of the invention are described in connection with the following illustrative drawings in which like numerals reference like elements, and wherein.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Aspects of the invention relate to controllably depositing a sample material on a work surface. In the illustrative embodiments described below, the sample material includes a liquid and the sample material is deposited in a droplet form. However, it should be understood that the sample material need not be or include a liquid, but instead may be or include a solid. Moreover, the sample material may include one element or composition, or include a combination of two or more elements or compositions. For example, the sample material may be a mixture of DNA or other genomic fragments in a liquid carrier material. In short, not all aspect of the invention are limited to depositing any particular type of sample material.

Figure 1:
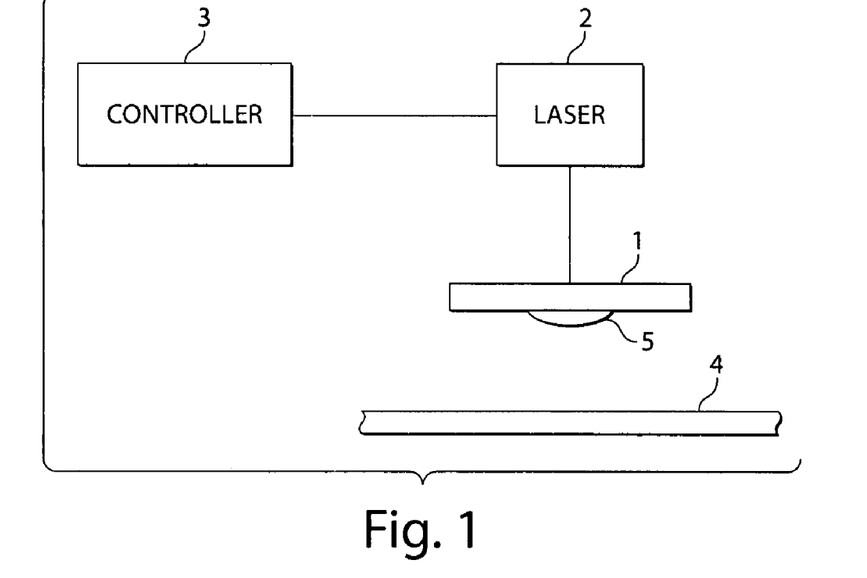
FIG. 1 is a sample deposition apparatus in accordance with one aspect of the invention.

FIG. 1 shows a sample depositing system in accordance with one aspect of the invention. In this illustrative embodiment, a sample transfer device 1 cooperates with an illumination source 2, such as a laser, and a controller 3 to controllably deposit at least a portion of a sample material 5 on a work surface 4. In this embodiment, the sample material 5 is carried by the sample transfer device 1 on a surface nearest the work surface 4 although the sample material 5 may be positioned in any suitable way relative to the sample transfer device 1 as will be discussed in more detail below. The work surface 4 is shown as being a flat, planar surface, but the work surface 4 may have any suitable form, such as a microtiter plate or a similar device having multiple wells or other sample holders, an absorbent material, or other suitable device or region to receive the sample material 5.

The sample transfer device and the way in which the sample material is associated with the sample transfer device 1 operate to deposit at least a portion of the sample material 5 on the work surface 4 upon suitable illumination from the illumination source 2. For example, illumination of the sample transfer device 1 may cause a portion of the sample transfer device 1 to move and thereby expel a droplet of the sample material 5. In another illustrative embodiment, illumination of the sample transfer device 1 can heat a portion of the sample transfer device 1 and/or the sample material 5 which causes deposition of a portion of the sample material 5 to occur. For example, a portion of the sample material 5 may heat rapidly in response to the illumination, causing a vapor bubble to form and thereby cause a droplet of the sample material 5 to be expelled. In another illustrative embodiment, illumination of the sample transfer device can transfer kinetic or other energy from the illumination to a portion of the sample material 5 and cause separation of at least a portion of the sample material from the sample transfer device 1. For example, the sample material 5 may include a material that, when illuminated by the beam 2, has atomic or other bonds that break and release energy to cause a portion of the sample material to be expelled. In another embodiment, adhesive or cohesive bonds between portions of the sample material 5 and/or the sample transfer device 1 may be broken by illumination of the beam, causing a portion of the sample material to be separated and deposited. Whatever the mechanism for deposition, however, illumination of the sample transfer device 1 does not cause a portion of the sample transfer device 1 on a side near the sample material 5 to break away and carry a portion of the sample material 5 with it.

The illumination provided by the illumination source 2 may be in any suitable form, in some cases depending upon the mechanism by which sample material is separated from the sample transfer device 1. For example, the illumination source 2 may be a laser, such as an YAG laser that emits a beam toward the sample transfer device 1. The illumination beam may be focused, collimated or have any other suitable form. Moreover, the beam may be steerable so that the beam illuminates selected portions of the sample transfer device 1. This may allow the illumination source 2 to address different portions of the sample transfer device 1 and control the positions at which sample material 5 is deposited on the work surface 4. For example, the sample transfer device 1 may include several areas where a sample material 5 is carried. The illumination source 2 may selectively illuminate these separate portions of the sample transfer device 1 so that the sample material is deposited into selected wells or other defined areas of the work surface 4. Of course, the illumination source 2 need not include a laser, but may provide any suitable visible or invisible electromagnetic illumination. In addition, the illumination source 2 may provide two or more beams that may be emitted simultaneously or sequentially, as desired.

The controller 3 may include any suitable components for performing sample deposition functions. For example, the controller 3 may include any suitable general purpose data processing system, which can be, or include, a suitably programmed general purpose computer or network of computers and other associated devices including communication devices, and/or other circuitry or components necessary to control operation of the illumination source 2. In addition, the controller 3 may control devices that move the sample transfer device 1 and/or the work surface 4, e.g., where such movement is used to control the position where sample material is deposited. Thus, the controller 3 may include robotic manipulators or other drives to move the illumination source 2, the sample transfer device 1 and/or the work surface 4. The controller 3 may also include other devices, such as an information display device (a printer, monitor or other device), user input devices (a keyboard, user pointing device, touch screen or other user interface), data storage devices (magnetic, optical or other memories), or other suitable devices.

Figure 2:
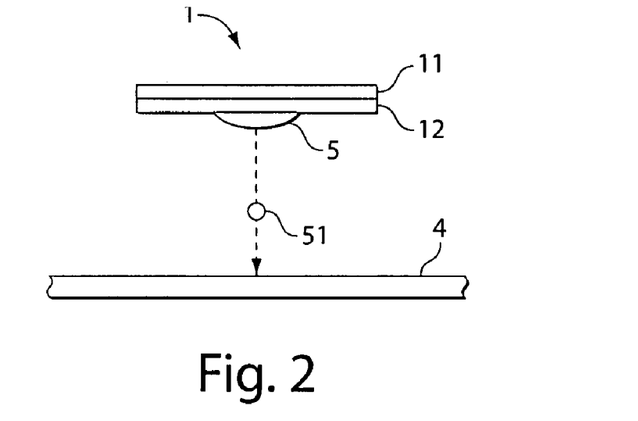
FIG. 2 shows a side view of a first embodiment of a sample transfer device emitting a sample droplet.

FIG. 2 shows one illustrative embodiment of a sample transfer device 1 having at least two layers 11 and 12 and a movable portion. A first layer 11 may include a first material such as a material that is transparent or translucent to the illumination beam from the illumination source 2. For example, the first layer 11 may include a quartz material, a plastic or other suitable material. A second layer 12 may include a material that is opaque to or otherwise impedes passage of the illumination through the sample transfer device 1. In this embodiment, the second layer 12 may include a metallic material, such as nickel or aluminum, a ceramic material, a liquid material, a gel, a plastic material or other suitable material. Upon illumination of the sample transfer device by an illumination beam, a portion of the sample transfer device 1 may move, causing a droplet 51 to be formed from the sample material 5 and deposited on the work surface 4. However, during movement of a portion of the sample transfer device 1, no portion of the sample transfer device 1 breaks away on a side near the sample material 5 to carry a portion of the sample material 5 (e.g., in a shrapnel-like effect) or otherwise cause deposition of the sample material 5. Instead, in this embodiment, the sample transfer device 1 stays generally intact while a portion of the device 1 moves to cause deposition.

Figure 3:
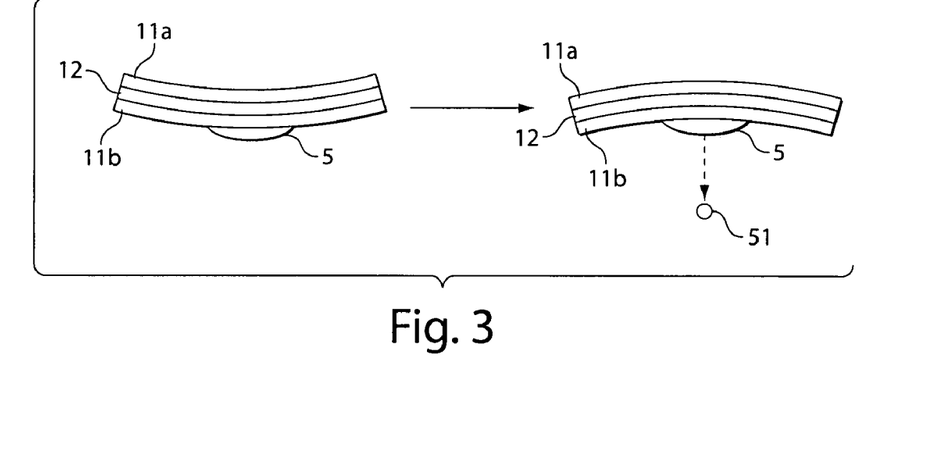
FIG. 3 shows a side view of another illustrative embodiment of a sample transfer device emitting a sample droplet.
Figure 4:
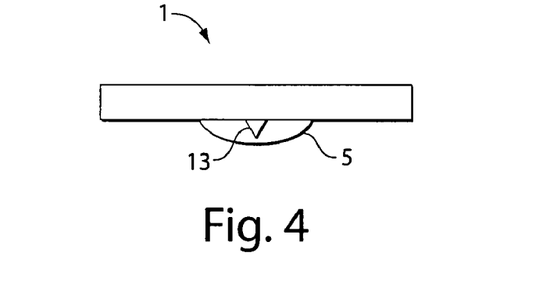
FIG. 4 shows a side view of another illustrative embodiment of a sample transfer device having a projection extending into a sample material.
Figure 5:
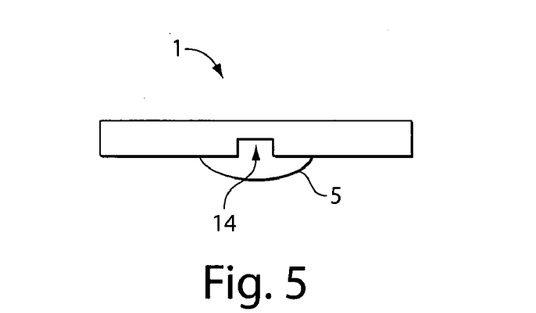
FIG. 5 shows a side view of yet another embodiment of a sample transfer device having a nozzle-like cavity.
Figure 6:
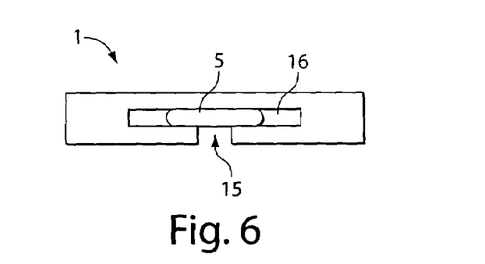
FIG. 6 shows a side view of another illustrative embodiment of a sample transfer device having an internal cavity from which a sample material is expelled.
Figure 7:
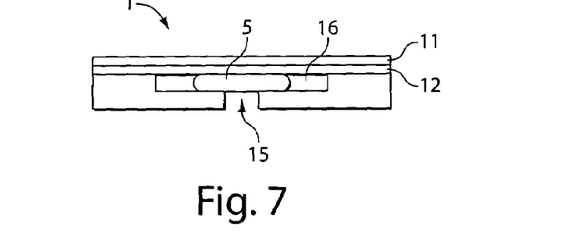
FIG. 7 shows a side view of another illustrative embodiment of a sample transfer device having an internal cavity and a moveable driver member.
Figure 8:
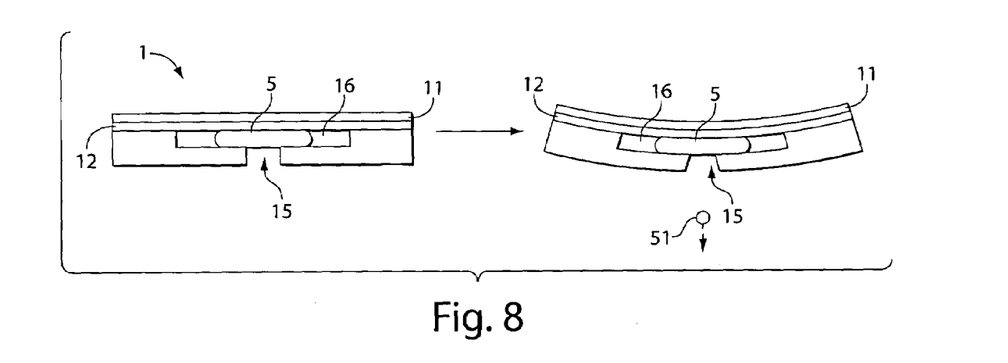
FIG. 8 illustrates a sample droplet being expelled from the FIG. 7 embodiment.

FIG. 3 shows another illustrative embodiment and a mechanism by which a sample transfer device 1 may operate to expel a droplet 51 from the sample material 5. This embodiment is different from the FIG. 2 embodiment in that the second layer 12 of opaque or transmission-resistant material has a first layer 11*a* of a transparent or translucent material on a top side and a third layer 11*b* of a material on a bottom side. The third layer 11*b* may separate the second layer 12 from the sample material 5 (e.g., to prevent the second layer 12 from contaminating or otherwise contact the sample material 5), and may or may not operate with the first and second layers 11*a* and 12 to cause deposition of a portion of sample material. However, the principles of operation of the FIG. 3 embodiment may apply to the FIG. 2 embodiment.

Prior to illumination, the sample transfer device 1 may be slightly concave up or flat with the sample material carried by the device 1 on a lower surface, as shown on the left in FIG. 3. Upon illumination, the sample transfer device 1 may move from the concave up or flat position to a concave down or flat position, as shown on the right in FIG. 3. This movement may cause a droplet 51 to be formed from the sample material 5 whereupon the droplet 51 is deposited on the work surface 4. Movement of the sample transfer device 1 may be caused, for example, by uneven expansion rates of the first and second layers 11*a* and 12 (or the second and third layers 12 and 11*b*, or the first, second and third layers 11*a*, 12, and 11*b*) when heated by the illumination beam. For example, depending on the geometry of the sample transfer device 1, the first layer 11*a* may expand more rapidly or more slowly than the second layer 12 in response to the illumination beam. This difference in expansion rates may cause the sample transfer device 1 to rapidly move or buckle causing the droplet 51 to be formed. However, the different expansion generally will not cause portions of the sample transfer device 1 to break away or otherwise separate on a side near the sample material 5. Although heating may be caused directly by the illumination beam, heating may be caused indirectly, e.g., by the beam activating an optically-controlled switch that allows current to flow through an electrical resistance heater in or on the sample transfer device 1.

FIGS. 2 and 3 show that the sample transfer device 1 has an approximately planar profile, but it should be understood that the sample transfer device 1 need not necessarily be made in a planar form. In addition, the sample transfer device 1 may have any suitable shape or configuration as viewed from the top, i.e., a direction parallel to the direction in which the droplet 51 is expelled as shown in FIGS. 2 and 3. For example, the sample transfer device 1 may have a rectangular, circular or other shape. Moreover, the layers 11 and 12 and other additional layers need not be formed continuously across the entire sample transfer device 1. Instead, the layers may be formed in a discontinuous or other suitable pattern. For example, the second layer 12 including the metallic material may be provided in concentric annular rings, parallel strips, or other suitable patterns. In addition, the sample transfer device 1 need not move upward to expel a drop as shown in FIG. 3, but instead may move downward, sideways or in another fashion to expel a droplet 51. Likewise, the sample transfer device need not expel drops only in a downward direction (with the force of gravity), but instead may deposit sample material in an upward or sideways direction. For example, expelling a drop upward (against the force of gravity on the drop) may allow for more control of the size, volume and/or weight of drops deposited on the work surface. That is, excessively large drops may not have sufficient energy when expelled to overcome the force of gravity and reach the work surface. Thus, only drops of a certain size or smaller may be successfully deposited. In addition, expelling drops upwardly may allow for easier positioning of sample material 5 on the sample transfer device, e.g., in some applications liquid sample material 5 may not be easily positioned on a bottom surface of a sample transfer device as shown in FIG. 1, and instead may be easier placed on a top side of the sample transfer device 1.

FIG. 4 shows another illustrative embodiment of a sample transfer device 1 having at least one projection 13. The projection 13 may function to help in separating a portion of the sample material 5 from the sample transfer device 1. For example, the projection 13 may serve a mechanical function to help in forming a droplet 51, e.g., by forming a discontinuity in the surface in the sample material 5 that helps to form a droplet 51. Alternately, the projection 13 may perform an optical function, e.g., by focusing illumination from the illumination source 2 to a particular portion of the sample transfer device 1 and/or the sample material 5. Focusing of the illumination may cause more rapid heating in selected locations and/or serve to more efficiently transfer kinetic or other energy from the beam to portions of the sample material 5. In another illustrative embodiment, the projection 13 may perform a heating function, e.g., where the projection 13 is arranged to be rapidly heated by the illumination beam and to conduct its heat to the sample material 5. This heat transfer may in turn heat the sample material 5, forming a bubble that causes a droplet 51 to be expelled. The projection 13 may have any suitable shape, which may depend upon the function that it performs in the sample transfer device 1. Similarly, the sample transfer device 1 may have multiple layers of different material, e.g., as in FIG. 2 or 3, or have any other suitable configuration.

FIG. 5 shows another illustrative embodiment of a sample transfer device 1 having at least one cavity 14. One or more cavities 14 in the sample transfer device 1 may aid in the formation of droplets expelled from the sample transfer device 1. For example, a cavity 14 may serve to focus or otherwise direct pressure waves in a liquid sample material 5 when one or more portions of the sample transfer device 1 moves, e.g., in a way like that shown in FIG. 3. The focusing or other effect on pressure waves may help form a droplet 51 when depositing a sample. Alternately, a cavity 14 may serve to preferentially heat one portion of the sample transfer device 1 or the sample material 5. For example, the cavity 14 may increase the surface area of the sample transfer device 1 in contact with the sample material 5, thereby increasing the heat transfer and consequent formation of a droplet 51 to be expelled. The cavity 14 may have any suitable size and/or shape depending on the function it performs. Moreover, the sample transfer device 1 may have two or more cavities 14 that may be individually addressed by the illumination source 2 or may otherwise individually form droplets 51 that are expelled from the sample transfer device 1. Like the projections 13 in FIG. 4, one or more cavities 14 may be incorporated in any type of sample transfer device, including those having two or more layers. Moreover, projections 13 and cavities 14 may be combined into single device and work together to deposit sample material 5.

FIG. 6 shows another illustrative embodiment of a sample transfer device 1 having an internal chamber 16 and an opening 15. In this illustrative embodiment, a sample material 5 is located in the chamber 16. The sample material 5 may or may not entirely fill the chamber 16. Upon illumination of the sample transfer device I, at least a portion of the sample material 5 may be expelled through the opening 15 and deposited on a work surface 4. The cause of the sample material 5 being forced through the opening 15 may be any of those described above, namely a heating of the sample material 5 or gas or other material in the chamber 16, movement of one or more portions of the sample transfer device I, or a transfer of kinetic or other energy from the illumination beam to portions of the sample material 5. For example, FIG. 7 shows one illustrative embodiment in which an upper portion of the sample transfer device 1 includes first and second layers 11 and 12 like that in the FIG. 2 embodiment. As can be seen in FIG. 8, illumination of the sample transfer device 1 may cause the first and second layers 11 and 12 to move from a rest position to a deflected position, e.g., a concave up condition shown in FIG. 8, which forces sample material in the chamber 16 through the opening 15. As with other illustrative embodiments, the sample transfer device may include multiple chambers 16 with multiple openings 15 from which droplets 51 may be expelled. Alternately, the sample transfer device 1 may be provided with one relatively large chamber 16 that communicates with two or more openings 15 through which droplets are expelled.

Figure 9:
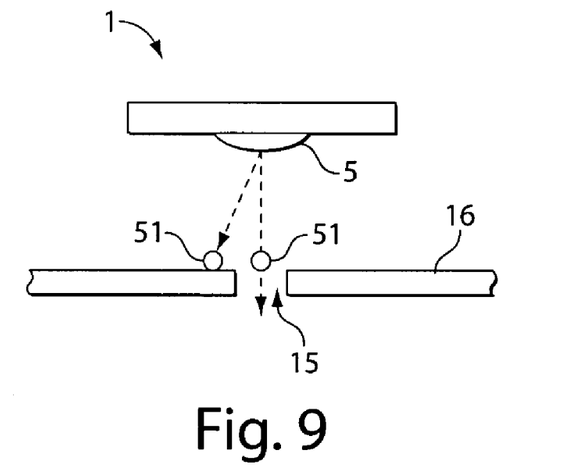
FIG. 9 shows an illustrative embodiment including a mask that defines at least one location where sample material is deposited on a work surface.

In another illustrative embodiment shown in FIG. 9, a mask 16 may be provided with a pattern of openings 15 and the sample transfer device 1 may expel sample material 5 in the general direction of the mask. The mask 16 may then selectively block portions of the sample material expelled by the sample transfer device 1, only allowing sample material to be deposited through the openings 15 in the mask 16 and onto desired locations on the work surface 4. The mask 16 may be secured to the sample transfer device 1, or may be separate.

Figure 10:
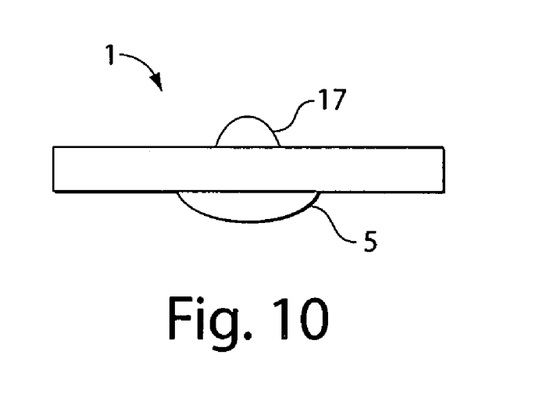
FIG. 10 shows an illustrative embodiment of a sample transfer device including an explosive or other reactive substance.

In another illustrative embodiment shown in FIG. 10, the sample transfer device 1 may have an explosive or other reactive substance or substances 17 on a portion of the sample transfer device 1. This substance 17 may explode or expand rapidly upon illumination of the illumination beam, thereby transferring kinetic energy to the sample transfer device 1. The explosion or rapid expansion may cause a portion of the sample transfer device 1 to move and cause a deposition of the sample material 5. The substance 17 may be provided in discrete locations on the sample transfer device 1 and selectively illuminated, the substance may be provided in a continuous layer and selectively illuminated, or other.

Various aspects of the invention may be particularly useful in depositing liquid samples of genomic, proteomic or other materials used in biotech research. Extremely small volume droplets may be produced using various aspects of the invention, with droplet volumes ranging down to the nanoliter size range. Aspects of the invention also allow sample deposition to occur with few moving parts and limited contact between the sample and the deposition apparatus.

While the invention has been described with reference to various illustrative embodiments, the invention is not limited to the embodiments described. It is evident that many alternatives, modifications and variations of the embodiments described will be apparent to those skilled in the art. Accordingly, embodiments of the invention as set forth herein are intended to be illustrative, not limiting. Various changes may be made without departing from the invention.

The invention claimed is:

1. A sample depositing system comprising:

an illumination source that forms an illumination beam;

a sample transfer device that receives the illumination beam from the illumination source, the sample transfer device including a portion constructed and arranged to move in response to suitable illumination incident on the sample transfer device;

a sample material carried by the sample transfer device; and a controller that causes the illumination source to illuminate the sample transfer device and thereby cause the portion of the sample transfer device to move, movement of the portion of the sample transfer device causing at least a portion of the sample material carried by the sample transfer device to be controllably separated from the transfer device and deposited on a work surface, the portion of sample material being deposited without any part of the sample transfer device positioned adjacent the sample material separating from the sample transfer device.

2. The system of claim 1, wherein the sample transfer device includes:

at least one layer of a material that is translucent or transparent to the illumination beam; and at least one layer of a material that is opaque to or substantially impedes transmission of the illumination beam.

3. The system of claim 1, wherein the sample transfer device includes:

at least one layer of a transparent material that is transparent to the illumination beam; and p1 at least one layer of an opaque material that is opaque to the illumination beam.

4. The system of claim 3, wherein the layer of transparent material and the layer of opaque material are positioned adjacent to each other and the adjacent layers are constructed and arranged to move in response to illumination from the illumination beam.

5. The system of claim 3, wherein the at least one layer of opaque material is separated from the sample material by a plastic material.

6. The system of claim 3, wherein the opaque material includes one of a plastic, a metal, a ceramic, a liquid material and a gel.

7. The system of claim 3, wherein the at least one layer of opaque material is surrounded by a plastic material.

8. The system of claim 1, wherein the sample material includes a liquid material.

9. The system of claim 1, wherein the sample material is carried by the sample transfer device on a side of the sample transfer device opposite the illumination source.

10. The system of claim 1, wherein the sample transfer device includes a metal layer surrounded by a clear plastic material.

11. The system of claim 1, wherein the portion of sample material is separated from the sample transfer device in droplet form.

12. The system of claim 1, wherein the illumination source includes a laser.

13. The system of claim 1, wherein the sample transfer device includes a chamber that communicates with an opening, and at least a portion of the sample material is located in the chamber.

14. The system of claim 1, wherein the sample transfer device includes at least one of a projection and a cavity constructed and arranged to aid in formation of a droplet of sample material.

15. The system of claim 1, further comprising a mask having at least one opening, the at least one opening defining a location in which sample material is deposited on a work surface.

16. The system of claim 1, wherein the sample transfer device includes a substance that explodes or expands rapidly upon illumination by the illumination beam and causes the portion of the sample transfer device to move.

17. The system of claim 1, wherein the portion of sample material being deposited moves in a direction generally against a force of earth's gravity and away from the sample transfer device.

18. A method for depositing a sample material, comprising:
  providing a sample material on a sample transfer device, the sample transfer device having a portion that moves in response to suitable illumination incident on the sample transfer device;

illuminating the sample transfer device with an illumination beam;

causing the portion of the sample transfer device to move so that at least a portion of the sample material is separated from the sample transfer device and deposited on a work surface in response to illumination of the illumination beam, the portion of the sample material being deposited without any portion of a surface positioned adjacent the sample material separating from the sample transfer device.

19. The method of claim 18, wherein the step of causing includes moving at least a portion of the surface in response to illumination of the illumination beam.

20. The method of claim 18, wherein the step of causing includes transferring energy from the illumination beam to the sample material.

21. The method of claim 18, wherein the step of causing includes heating a portion of the sample material by the illumination beam.

22. The method of claim 18, wherein the step of providing a sample material on a surface includes providing the sample material in a chamber that communicates with an opening, and the step of causing includes causing a portion of the chamber to move in response to illumination by the illumination beam and expelling a portion of the sample material through the opening.

23. The method of claim 18, further comprising providing a mask having at least one opening, the at least one opening defining a location in which sample material is deposited on a work surface, and the step of causing includes expelling a portion of the sample material in a direction toward the mask.

24. The method of claim 18, wherein the step of providing a sample material includes providing a sample transfer device having at least one layer of a material that is optically translucent or transparent to the illumination beam, and at least one layer of a material that is opaque to or substantially impedes transmission of the illumination beam.

25. The method of claim 24, wherein the step of providing a sample material includes providing a sample transfer device having at least one layer of a transparent material that is transparent to the illumination beam, and at least one layer of an opaque material that is opaque to the illumination beam.

26. The method of claim 25, wherein the step of causing includes moving the adjacent layers in response to illumination from the illumination beam.

27. The method of claim 25, wherein the step of providing a sample material includes providing a liquid sample material on a surface of the sample transfer device.

28. A sample depositing a system comprising:

a sample transfer means for carrying a sample material, the sample transfer means including a portion that moves in response to suitable illumination incident on the sample transfer means;

means for illuminating the means for carrying with an illumination beam; and means for causing the portion of the sample transfer device to move so that at least a portion of the sample material is separated from the sample transfer means and deposited on a work surface in response to illumination of the illumination beam, the portion of the sample material being deposited without any part of the sample transfer means positioned adjacent the sample material separating from the sample transfer means.

* * * * *

UNITED STATES PATENT AND TRADEMARK OFFICE
CERTIFICATE OF CORRECTION

PATENT NO. : 7,438,859 B2
APPLICATION NO. : 10/750377
DATED : October 21, 2008
INVENTOR(S) : Peter Massaro Page 1 of 1

It is certified that error appears in the above-identified patent and that said Letters Patent is hereby corrected as shown below:

In the Specification:

Col. 7, line 6, please delete "I" and insert --1--

In the Claims:

Claim 3, Col. 8, line 31, please delete "p1"

Signed and Sealed this

Sixteenth Day of December, 2008

JON W. DUDAS
*Director of the United States Patent and Trademark Office*